United States Patent
Miller et al.

(10) Patent No.: US 11,896,284 B2
(45) Date of Patent: *Feb. 13, 2024

(54) SYSTEM AND METHOD FOR MEASUREMENT OF AN IMPEDANCE USING A CATHETER SUCH AS AN ABLATION CATHETER

(71) Applicant: St. Jude Medical, Atrial Fibrillation Division, Inc., St. Paul, MN (US)

(72) Inventors: Stephan P. Miller, Minneapolis, MN (US); Glen H. Kastner, Saint Michael, MN (US); Donald Curtis Deno, Andover, MN (US)

(73) Assignee: St. Jude Medical, Atrial Fibrillation Division, Inc, St. Paul, MN (US)

( * ) Notice: Subject to any disclaimer, the term of this patent is extended or adjusted under 35 U.S.C. 154(b) by 860 days.

This patent is subject to a terminal disclaimer.

(21) Appl. No.: 16/851,441

(22) Filed: Apr. 17, 2020

(65) Prior Publication Data

US 2020/0237426 A1 Jul. 30, 2020

Related U.S. Application Data

(63) Continuation of application No. 11/966,232, filed on Dec. 28, 2007, now Pat. No. 10,660,690.

(51) Int. Cl.
*A61B 18/14* (2006.01)
*A61B 18/12* (2006.01)
(Continued)

(52) U.S. Cl.
CPC ...... *A61B 18/1206* (2013.01); *A61B 18/1492* (2013.01); *A61B 2018/00577* (2013.01);
(Continued)

(58) Field of Classification Search
CPC ............ A61B 18/1206; A61B 18/1492; A61B 2018/00577
See application file for complete search history.

(56) References Cited

U.S. PATENT DOCUMENTS

| 4,641,649 A | 2/1987 | Walinsky |
| 5,224,939 A | 7/1993 | Holman et al. |
| (Continued) | | |

FOREIGN PATENT DOCUMENTS

| EP | 0889744 B1 | 1/2004 |
| EP | 1254641 B1 | 11/2008 |
| (Continued) | | |

OTHER PUBLICATIONS

Salazar, Transmural Versus Nontransmural In Situ Electrical Impedance Spectrum for Healthy, Ischemic, and Healed Myocardium, IEEE Transactions on Biomedical Engineering, vol. 51, No. 8, Aug. 2004.

(Continued)

*Primary Examiner* — Michael F Peffley
*Assistant Examiner* — Samantha M Good
(74) *Attorney, Agent, or Firm* — Kilpatrick Townsend & Stockton LLP

(57) ABSTRACT

A catheter and patch electrode system is provided for use with an apparatus, such as an ablation generator, having a 4-wire interface for improved impedance measurement. The 4-wire interface includes a pair of source connectors across which an excitation signal is produced and a pair of sense connector wires across which the impedance is measured. The RF ablation generator may also produce an ablation signal across a source wire and an indifferent return patch electrode. The system further includes a cable that connects the generator to a catheter. The catheter includes a shaft having a proximal end and a distal end, with an ablation tip (Continued)

electrode disposed at the distal end. A source lead is electrically coupled to the tip electrode and extends through the shaft to the proximal end where it is terminated. An optional sense lead is also electrically coupled to the tip electrode and extends through the shaft to the proximal end. The system further includes a source return (e.g., skin patch) and a sense return (e.g., skin patch), either or none of which may be combined with the indifferent return, and if used may be placed on opposite sides of the patient for improved performance. The impedance sensor circuit produces an excitation signal across the source connectors, which is then carried to the catheter by the cable, then to the tip electrode, travels through the complex load (tissue volume), and returns to the generator via a patch electrode. The impedance is measured by observing the voltage drop across the sense connectors caused by the excitation signal.

19 Claims, 11 Drawing Sheets

(51) Int. Cl.
  *A61B 18/00* (2006.01)
  *A61B 18/16* (2006.01)
(52) U.S. Cl.
  CPC ............. *A61B 2018/00875* (2013.01); *A61B 2018/165* (2013.01)

(56) References Cited

U.S. PATENT DOCUMENTS

| | | | |
|---|---|---|---|
| 5,297,549 A | 3/1994 | Beatty et al. | |
| 5,311,866 A | 5/1994 | Kagan et al. | |
| 5,341,807 A | 8/1994 | Nardella | |
| 5,380,301 A | 1/1995 | Prichard et al. | |
| 5,400,783 A | 3/1995 | Pomeranz et al. | |
| 5,447,529 A | 9/1995 | Marchlinski | |
| 5,456,254 A | 10/1995 | Pietroski et al. | |
| 5,562,721 A | 10/1996 | Marchlinski | |
| 5,626,136 A | 5/1997 | Webster, Jr. | |
| 5,636,990 A | 6/1997 | Stemmann | |
| 5,673,704 A | 10/1997 | Marchlinski | |
| 5,697,377 A | 12/1997 | Wittkampf | |
| 5,715,817 A | 2/1998 | Stevens-Wright et al. | |
| 5,715,832 A | 2/1998 | Koblish et al. | |
| 5,718,241 A | 2/1998 | Ben-Haim et al. | |
| 5,827,278 A | 10/1998 | Webster, Jr. | |
| 5,837,001 A | 11/1998 | Mackey | |
| 5,876,373 A | 3/1999 | Giba et al. | |
| 5,931,835 A | 8/1999 | Mackey | |
| 5,954,665 A | 9/1999 | Ben-Haim | |
| 6,045,550 A * | 4/2000 | Simpson ............ | A61B 18/1492 606/41 |
| 6,063,078 A | 5/2000 | Wittkampf | |
| 6,074,379 A | 6/2000 | Prichard | |
| 6,123,702 A | 9/2000 | Swanson et al. | |
| 6,179,824 B1 | 1/2001 | Eggers et al. | |
| 6,226,542 B1 | 5/2001 | Reisfeld | |
| 6,256,540 B1 | 7/2001 | Panescu | |
| 6,273,404 B1 | 8/2001 | Holman et al. | |
| 6,350,263 B1 | 2/2002 | Wetzig et al. | |
| 6,423,057 B1 | 7/2002 | He et al. | |
| 6,443,894 B1 | 9/2002 | Sumanaweera et al. | |
| 6,471,693 B1 | 10/2002 | Carroll | |
| 6,491,681 B1 | 12/2002 | Kunis et al. | |
| 6,511,478 B1 | 1/2003 | Burnside et al. | |
| 6,554,794 B1 | 4/2003 | Mueller et al. | |
| 6,690,963 B2 | 2/2004 | Ben-Haim et al. | |
| 6,752,804 B2 | 6/2004 | Simpson et al. | |
| 6,965,795 B2 | 11/2005 | Rock | |
| 7,004,937 B2 | 2/2006 | Lentz et al. | |
| 7,214,220 B2 | 5/2007 | McGlinch et al. | |
| 7,217,256 B2 | 5/2007 | Di Palma | |
| 7,263,397 B2 | 8/2007 | Hauck | |
| 7,608,063 B2 | 10/2009 | Le et al. | |
| 7,625,365 B2 | 12/2009 | McGlinch et al. | |
| 7,637,907 B2 | 12/2009 | Blaha | |
| 7,666,204 B2 | 2/2010 | Thornton et al. | |
| 7,959,601 B2 | 6/2011 | McDaniel et al. | |
| 8,221,390 B2 | 7/2012 | Pal et al. | |
| 8,273,016 B2 | 9/2012 | O'Sullivan | |
| 8,376,990 B2 | 2/2013 | Ponzi et al. | |
| 8,608,703 B2 | 12/2013 | Riles et al. | |
| 8,700,120 B2 | 4/2014 | Koblish | |
| 8,777,929 B2 | 7/2014 | Schneider et al. | |
| 8,814,824 B2 | 8/2014 | Kauphusman et al. | |
| 8,882,705 B2 | 11/2014 | McDaniel et al. | |
| 8,996,091 B2 | 3/2015 | de la Rama et al. | |
| 9,017,308 B2 | 4/2015 | Klisch et al. | |
| 9,247,990 B2 | 2/2016 | Kauphusman et al. | |
| 9,433,751 B2 | 9/2016 | Ponzi et al. | |
| 9,468,495 B2 | 10/2016 | Kunis et al. | |
| 9,694,159 B2 | 7/2017 | Schneider et al. | |
| 10,052,457 B2 | 8/2018 | Nguyen et al. | |
| 10,099,036 B2 | 10/2018 | Heideman et al. | |
| 10,660,690 B2 * | 5/2020 | Miller ............. | A61B 18/1206 |
| 2002/0049375 A1 | 4/2002 | Strommer et al. | |
| 2002/0077627 A1 | 6/2002 | Johnson et al. | |
| 2002/0165484 A1 | 11/2002 | Bowe et al. | |
| 2003/0045871 A1 | 3/2003 | Jain | |
| 2003/0093067 A1 | 5/2003 | Panescu | |
| 2003/0109871 A1 | 6/2003 | Johnson et al. | |
| 2003/0130711 A1 * | 7/2003 | Pearson ............. | A61B 18/1477 607/101 |
| 2004/0030258 A1 | 2/2004 | Williams et al. | |
| 2006/0271038 A1 | 11/2006 | Johnson | |
| 2007/0073179 A1 | 3/2007 | Afonso | |
| 2007/0100332 A1 | 5/2007 | Paul | |
| 2007/0123764 A1 | 5/2007 | Thao et al. | |
| 2007/0244479 A1 | 10/2007 | Beatty | |
| 2007/0255162 A1 | 11/2007 | Abboud et al. | |
| 2008/0234564 A1 | 9/2008 | Beatty et al. | |
| 2009/0171345 A1 | 7/2009 | Miller | |
| 2016/0213423 A1 | 7/2016 | Kauphusman et al. | |

FOREIGN PATENT DOCUMENTS

| | | |
|---|---|---|
| EP | 1690564 B1 | 4/2009 |
| EP | 1723981 B1 | 8/2010 |
| EP | 2018203 B1 | 6/2012 |
| EP | 1814450 B1 | 1/2013 |
| EP | 1968679 B1 | 9/2016 |
| EP | 1759668 B1 | 12/2018 |
| EP | 2155301 B1 | 4/2021 |
| JP | 0663056 A | 3/1994 |
| JP | 11502144 A | 2/1999 |
| JP | 2000501628 A | 2/2000 |
| JP | 2004500957 A | 1/2004 |
| JP | 2005144182 A | 6/2005 |
| JP | 4545384 B2 | 7/2010 |
| JP | 4887810 B2 | 2/2012 |
| JP | 5154031 B2 | 2/2013 |
| JP | 5193190 B2 | 5/2013 |
| JP | 5372314 B2 | 12/2013 |
| JP | 5908270 B2 | 4/2016 |
| JP | 5944331 B2 | 7/2016 |
| WO | 1995018576 | 7/1995 |
| WO | 9843530 A1 | 10/1998 |
| WO | 0168178 A1 | 9/2001 |
| WO | 2007067628 | 6/2007 |
| WO | 2007067941 | 6/2007 |
| WO | 2008091197 A1 | 7/2008 |

OTHER PUBLICATIONS

Gales, Use of Bioelectrical Impedance Analysis to Assess Body Composition of Seals, Marine Mammal Science 10 (1), 1-12 (Jan. 1994), doi:10.1111/j.1748-7692.1994.tb00385.x.

(56) References Cited

OTHER PUBLICATIONS

Cho, Design of Electrode Array for Impedance Measurement ofoLesions in Arteries, Physiol. Meas. 26 (2005) S19- S26, doi: 10.1088/0967-3334/26/2/002.
Fenici et al., Biomagnetically Localizable Multipurpose Catheter and Method for MCG Guided Intracardiac Electrophysiology, Biopsy and Ablation of Cardiac Arrhythmias, Int'l Journal of Cardiac Imaging 7: 207-215, 1991.
Masse et al., A Three-Dimensional Display for Cardiac Activation Mapping, PACE, p. 538, vol. 14; Apr. 1991.
International Search Report and Written Opinion for PCT/US2008/084200 dated Jan. 22, 2009.
International Search Report and Written Opinion for PCT/US2008/084194 dated Feb. 5, 2009.

\* cited by examiner

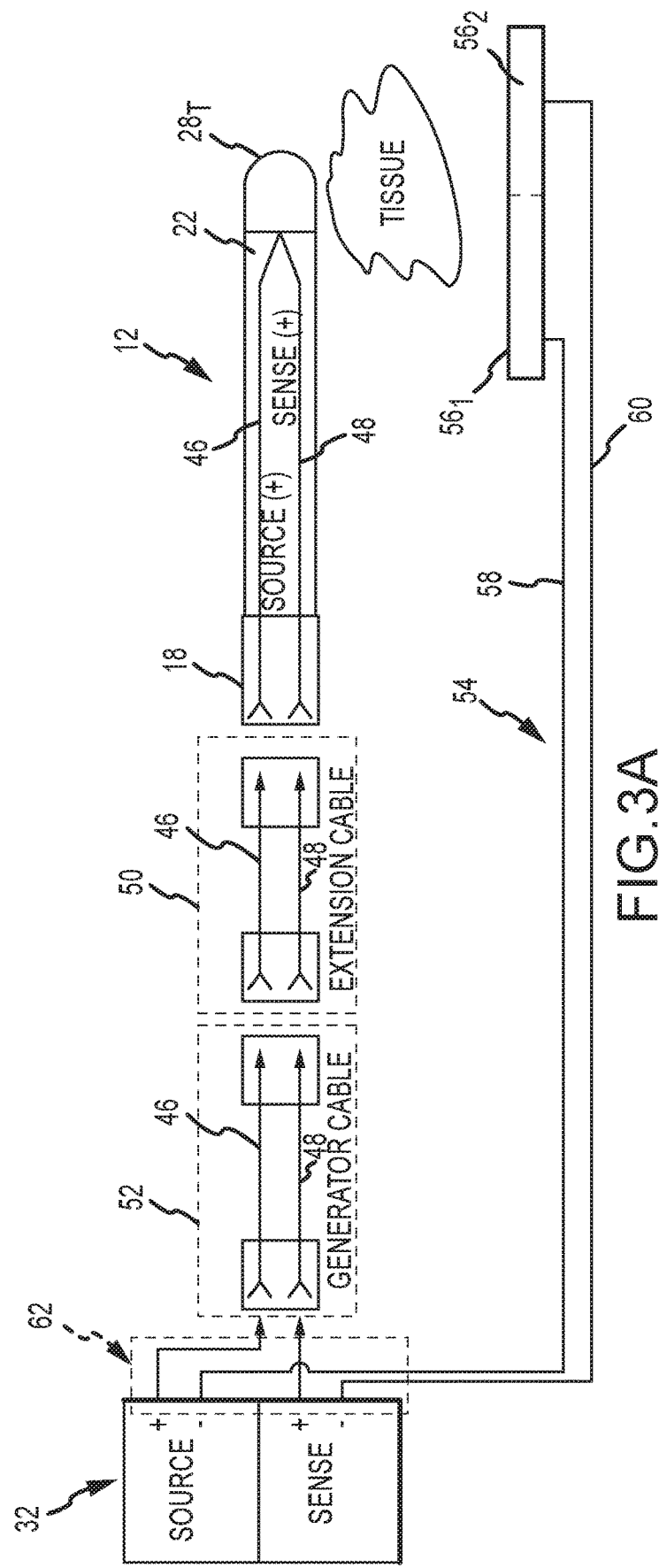

SYSTEM AND METHOD FOR MEASUREMENT OF AN IMPEDANCE USING A CATHETER SUCH AS AN ABLATION CATHETER

CROSS REFERENCE TO RELATED APPLICATIONS

This application is a continuation of U.S. application Ser. No. 11/966,232, filed 28 Dec. 2007 (now U.S. Pat. No. 10,660,690). The disclosure which is hereby incorporated by reference as though fully set forth herein.

BACKGROUND OF THE INVENTION a. Field of the Invention

The instant invention relates to a system and method for measuring an impedance using an ablation catheter.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature and to the intended site, for example, a site within the patient's heart, and carries one or more electrodes, which may be used for mapping, ablation, diagnosis, or other treatments.

There are a number of methods used for ablation of desired areas, including, for example, radio frequency (RF) ablation. RF ablation is accomplished by transmission of radio frequency energy to a desired target area through an electrode assembly to ablate tissue at the target site. RF ablation may generate excessive heat if not controlled. It is therefore known to provide an ablation generator with certain feedback features, such as temperature and impedance. To provide such feedback for the physician/clinician's use during the procedure, conventional RF ablation generators are typically configured to measure and display a magnitude of a complex impedance (Z) at least intended to represent the impedance of the patient's tissue proximate the ablation electrode. To make the impedance measurement, conventional generators use one tip conductor (i.e., one lead through the catheter to the ablation tip electrode) and one RF indifferent/dispersive return (i.e., one lead from the RF indifferent return going back to the generator)—a two terminal configuration for measurement. The frequency of the source used to make the impedance measurement is generally the ablation energy source frequency, which typically may be around 450 kHz or higher depending on the ablation generator. Such impedance measurements are commonly used to assess tissue heating and tissue-electrode contact. However, one shortcoming in the art is that such two-terminal measurements are subject to variation in the measurement of impedance due to factors unrelated to the condition of the tissue (i.e., non-physiologic changes). For example, coiling of an ablation cable that connects the ablation generator to the catheter can alter the impedance measurement, providing an inaccurate reading that is not completely indicative of the actual tissue condition.

Other impedance measurement techniques are known generally. For example, four-terminal measurements have been considered for the measurement of bulk bioelectrical impedance and measurement of lesions in arteries. However, these other measurement techniques do not address the problems described above.

There is therefore a need to minimize or eliminate one or more of the problems set forth above.

BRIEF SUMMARY OF THE INVENTION

It is desirable to be able to provide a technique for measuring an impedance of tissue using a catheter, such as an intra-cardiac ablation catheter. One advantage of the present invention is that it provides an impedance measuring system that is relatively immune to environmental changes unrelated to a patient, such as cable length, coiling and the like. Another advantage is that it provides for an accurate assessment of complex impedance, which has a wide variety of uses in diagnostic and therapeutic procedures. The present invention provides a four-wire (i.e., positive and negative source wires for producing an excitation signal and positive and negative sense wires for measuring the resultant impedance), three-terminal measurement arrangement for measuring impedance that is more robust than conventional two-wire, two-terminal approaches.

In one embodiment, a system is provided that is suitable for use with an apparatus that has a four-wire interface comprising a pair of source connectors (positive and negative) and a pair of sense connectors (positive and negative). While this apparatus may be a stand-alone unit, the invention allows for combination with other equipment, such as a radio frequency (RF) ablation generator. The system includes a catheter having a tip electrode, a source return and a sense return (e.g., the returns may be conductive patches suitable for affixation to the body). In practical RF ablation embodiments, an RF indifferent (dispersive) return (electrode) would also be provided to cooperate with the ablation tip electrode. The catheter includes an elongated shaft having a proximal end and a distal end. The tip electrode is disposed at the distal end. A source lead is electrically connected to the tip electrode and extends through the shaft of the catheter to its proximal end, where it is destined for connection to the positive source connector. The source and sense returns are configured for connection to respective negative source and sense connectors at the apparatus. The apparatus is configured to produce an excitation signal across the source connectors. The excitation signal is an alternating current (AC) signal whose frequency is preferably selected, in RF ablation embodiments, so as to not interfere with the RF ablation frequency. The excitation signal, when applied by way of the tip electrode, will result in a response signal, which is measured across the sense connectors and used in determining the complex impedance of the tissue proximate the tip electrode. For example, when the excitation signal is a constant current AC signal, an AC voltage signal is produced in response over the complex load (i.e., tissue), which is then measured across the sense connectors.

In a further embodiment, the source and sense returns are combined in a single patch with separate sections of conductive material. In a still further preferred embodiment, however, the source and sense returns are in separate patches that are spaced apart by a predetermined distance. Still more preferably, these two patches are located on opposite sides of a patient so as to maximize the predetermined distance. In either case (single patch/two patches), the tip electrode defines a first terminal while the separate source/sense returns defines the second and third terminals, respectively. As described in greater detail herein, this four-wire, three-terminal measurement arrangement provides for improved performance in determining the complex impedance in the tissue volume proximate the tip electrode.

In a still further embodiment, the system includes a cable (i.e., supply cable) having a first end configured for connection to the apparatus (e.g., RF ablation generator) and a second end configured for connection to the catheter. The cable has a source conductor and a separate sense conductor. The source and sense conductors are terminated separately at the first end for respective, separate connections to the positive source and sense connectors. The source and sense conductors are electrically joined (with each other) at the second end for a single connection to the source lead of the catheter, which runs to the tip electrode. In this embodiment, a single lead through the catheter is used for impedance measurements.

In addition, a two-lead catheter according to the invention is also presented. In a still further embodiment, one of the source or sense returns is combined with the RF indifferent return mentioned above (i.e., that is to be used for the RF ablation) and a catheter ring electrode is used for the other one of the source/sense returns. Still other variations are presented.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3A is a simplified diagrammatic and block diagram of a first four-wire embodiment using a two-lead catheter and a single-patch configuration.

DETAILED DESCRIPTION OF THE INVENTION

Figure 1:
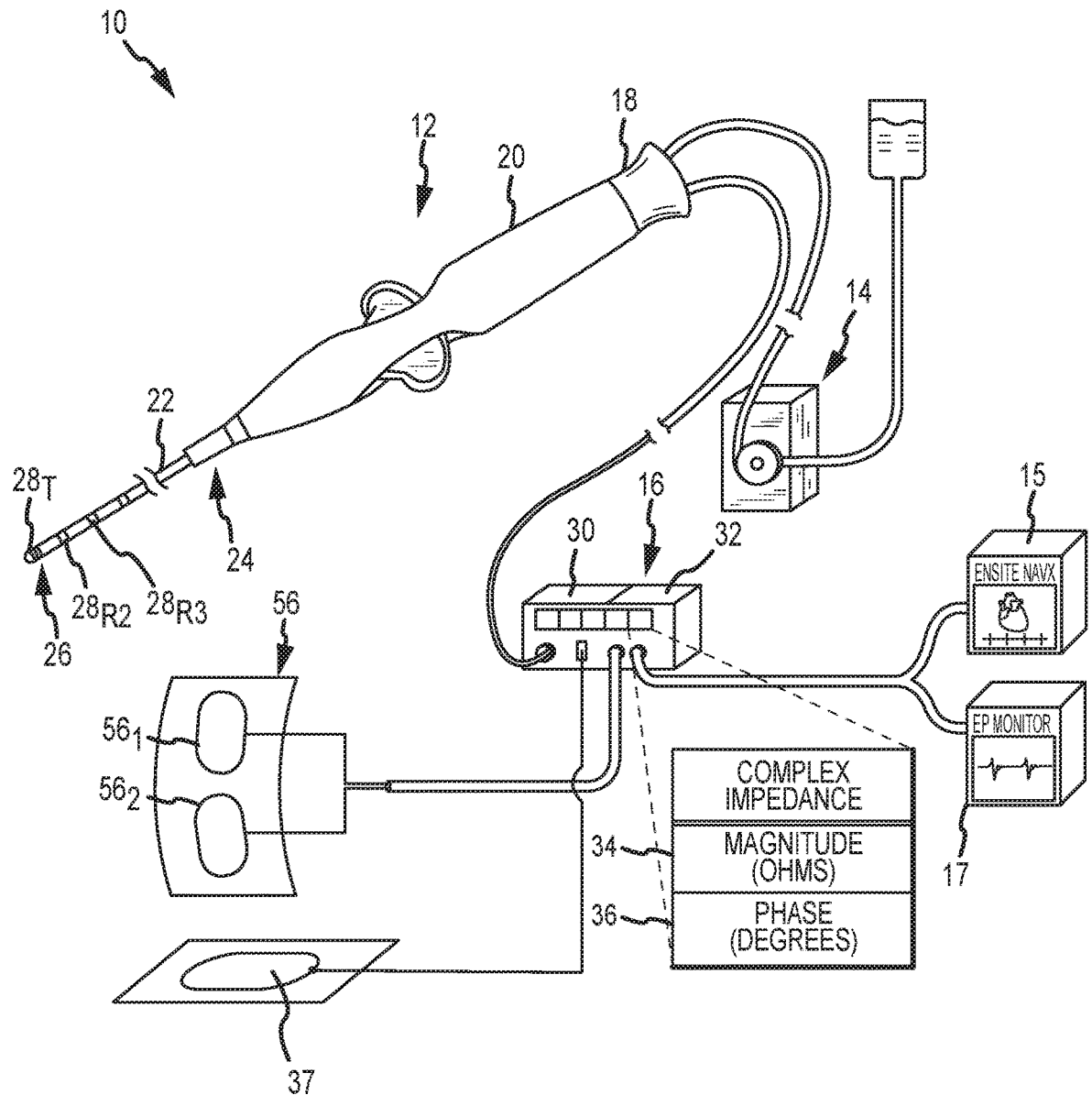
FIG. 1 is a diagrammatic view of an RF ablation embodiment having improved impedance determining function in accordance with the present invention.

Referring now to the drawings wherein like reference numerals are used to identify identical components in the various views, FIG. 1 is a simplified, perspective view of a system 10 for conducting a diagnostic or therapeutic function, which also includes an improved capability for measuring complex impedance. The illustrated embodiment shows an RF ablation configuration, and accordingly system 10 includes a catheter 12 operably connected to a fluid source 14, such as a pump assembly, and an energy source, such as an RF ablation generator 16. The fluid source 14 and the RF ablation generator 16 may serve to facilitate the operation of ablation procedures and may involve monitoring any number of chosen variables (e.g., temperature of ablation electrode, ablation energy, and position of the assembly), assisting in manipulation of the assembly during the use, and providing the requisite energy source. Furthermore, additional components may be integrated into the system 10, such as visualization, mapping and navigation components known in the art, including among others, for example, an EnSite NavX™ system 15 commercially available from St. Jude Medical, Inc., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. Additionally, an electrophysiological (EP) monitor or display such as an electrogram signal display 17, or other systems conventional in the art may also be integrated into the system 10. Moreover, it should be understood that embodiments consistent with the present invention may, and typically will, include other features not shown or described herein for the sake of brevity and clarity. For example, an ablation catheter may typically include additional electrodes (and corresponding leads), a temperature sensor (and corresponding leads), and other features as known in the art.

The catheter 12 may include a cable connector portion or interface 18, a handle 20 and a shaft 22 having a proximal end 24 and a distal end 26. In the illustrated embodiment, disposed on the shaft 22 near the distal end is an ablation tip electrode $28_T$. In addition, the shaft 22 may further include one or more other electrodes, configured for intra-cardiac use, such as a ring-2 electrode $28R_2$ and a ring-3 electrode $28R_3$. It should be re-iterated that the catheter 12 may include still other electrodes, and that in any event, in other embodiments (other than RF ablation), one or more electrodes may be used for any number of diagnostic and/or therapeutic purposes. For instance, such electrodes and therefore such catheters may be used for performing ablation procedures, cardiac mapping, electrophysiological (EP) studies, and other like procedures. Accordingly, the present invention is not limited to any one type of catheter or catheter-based system or procedure.

The general structural and functional features of catheter systems such as those generally comprising the catheter 12, the fluid source 14 and the RF ablation generator 16 are generally well known to those of skill in the art. For example, the fluid source 14 can comprise various known assembly, including fixed volume rolling pumps, variable volume syringe pumps and other pump assembly known to those skill in the art, including a gravity fed supply as shown. Moreover, the fluid provided by fluid source 14 may comprise a suitable biocompatible fluid, such as saline. Subject to the modification described below, the RF ablation generator 16 may comprise conventional apparatus, such as a commercially available unit sold under the model number IBI-1500T RF Cardiac Ablation Generator, available from Irvine Biomedical, Inc. Of course, the RF ablation generator 16 can also comprise various other known energy sources.

With continued reference to FIG. 1, the RF ablation generator 16 includes an RF ablation signal source 30 configured to generate an ablation signal that is output across a pair of source connectors (i.e., a positive polarity connector SOURCE (+) and a negative polarity connector SOURCE (−)—best shown in FIGS. 3A-3E).

The ablation generator 16 is further configured to generate an excitation signal that is also output across the source connectors. The excitation signal is used for determining the complex impedance. The ablation generator 16 further includes a complex impedance sensor 32 that is coupled to a pair of sense connectors (i.e., a positive polarity connector SENSE(+) and a negative polarity connector SENSE (−)—best shown in FIGS. 3A-3E). A corresponding RF indifferent/dispersive return 37 is shown, which acts as the electrical return for the RF ablation signal. The RF indifferent return 37 may comprise conventional construction and materials known in the art. Additionally, a patch 56, or a pair of separate patches may be provided in certain embodiments and which implement a source return $56_1$ and a sense return $56_2$, each being configured for respective connection at the SOURCE (−) and SENSE (−) connectors at the generator 16. The source and sense returns $56_1$ and $56_2$ included in the patch 56 (or patches) are formed of electrically conductive material to form a respective electrode. The patch 56 is configured for affixation to the body of a patient so that the returns make skin contact and thus electrical contact. Additionally, conventional wiring may be used as part of the source and sense returns to complete the connections to the SOURCE (−) and SENSE (−) connectors at the ablation generator 16.

The complex impedance sensor 32 is configured to determine an impedance, and optionally a complex impedance of a tissue volume proximate the tip electrode $28_T$. For frame of reference, complex impedance can be expressed in rectangular coordinates as set forth in equation (1):

$$Z = R + jX \qquad (1)$$

Where R is the resistance component (expressed in ohms); and X is a reactance component (also expressed in ohms). Complex impedance can also be expressed polar coordinates as set forth in equation (2):

$$Z = r \cdot e^{j\theta} = |Z| \cdot e^{j<Z} \qquad (2)$$

Where |Z| is the magnitude of the complex impedance (expressed in ohms) and $<Z=\theta$ is the phase angle expressed in radians. Alternatively, the phase angle may be expressed in terms of degrees where $\phi = 180/\pi \cdot \theta$.

Throughout the remainder of this specification, phase angle will be preferably referenced in terms of degrees. As used herein, the term complex impedance is taken to include a magnitude and a phase angle. Where a magnitude of the complex impedance is intended, the absolute value will be denoted, |Z|. As shown in exemplary fashion in FIG. 1, the complex impedance may comprise, in polar coordinates: a magnitude component 34 (i.e., |Z|, expressed in ohms) and a phase angle component 36 (i.e., $\phi$, expressed in degrees). The complex impedance, in a preferred embodiment, is derived from the excitation signal, in a manner more fully described below.

With continued reference to FIG. 1, in general, the RF ablation signal may typically have a frequency of 450 kHz or greater, although the present invention is not limited to this range. Additionally, the excitation signal may be an alternating current (AC) signal having a frequency preferably within a range of between about 2 kHz to 200 kHz, and more preferably about 20 kHz. In one embodiment, the excitation signal is a constant current signal, preferably in the range of between about 20-200 µA, and more preferably about 100 µA. A constant current AC excitation signal is configured to develop a corresponding AC response voltage signal depending on the complex impedance of the load. Variations in this regard are contemplated by the present invention, for example, the excitation signal may be an AC voltage signal where the response signal comprises an AC current signal. Nonetheless, a constant current excitation signal is preferred as being more practical.

It should be appreciated that the excitation frequency is outside of the frequency range of the RF ablation signal, which allows the complex impedance sensor 32 to distinguish the two signals, and facilitates filtering and subsequent processing of the AC response voltage signal. The excitation signal frequency is also preferably outside the frequency range of conventionally expected electrogram (EGM) signals in the frequency range of 0.05-1 kHz. Thus, in summary, the excitation signal preferably has a frequency that is above the typical EGM signal frequencies and below the typical RF ablation signal frequencies. Finally, it should be appreciated that the RF ablation signal source 30 and the complex impedance sensor 32 need not be incorporated into the same enclosure, although for a number of reasons, it may be commercially efficient to do so. It should be noted that in the illustrative embodiment, both the RF ablation signal and the excitation signal are generated across the same source connectors. Additionally, it should be understood that the term connectors (e.g., source connectors, sense connectors) should not imply any type of physical interface mechanism, but is rather broadly contemplated to represent one or more electrical nodes.

Figure 2A:
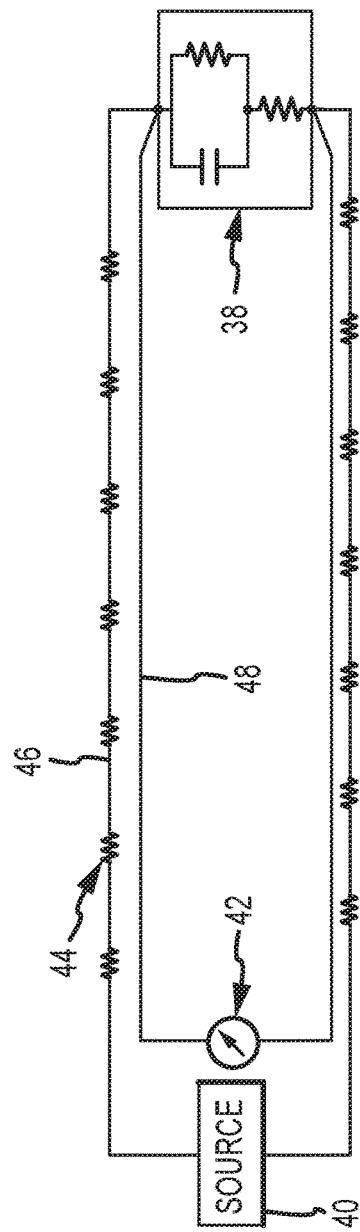
FIG. 2A is a simplified schematic diagram showing generally a four-wire, two-terminal approach for determining an impedance in accordance with the invention.

FIG. 2A is a simplified schematic diagram showing the concept of a four-wire, two-terminal impedance measurement arrangement. FIG. 2A shows a load 38 having a complex impedance, which load corresponds to the impedance of a tissue volume proximate a tip electrode and between the tip electrode and its return. FIG. 2A further shows an RF source 40, an impedance measuring meter 42, an incremental resistance 44 of a source line 46 and a sense line 48. The four-wire approach in general provides a first set of wires (source) for carrying the excitation signal and a second set of lines (sense) for detecting the complex impedance of the load. As described in the Background, any changes in cable resistance, inductance, etc., will cause phase measurement errors at the ablation generator (source 40 in the FIG. 2A) if only a two wire approach is used. Thus, different cables, extension cables, conversion cables, etc., may cause magnitude and phase measurement errors. Using a second set of wires (the sense line and its return) divorces the measurement of the impedance from the excitation signal (and the ablation signal as well), and improves the robustness of the impedance measurement.

Figure 2B:
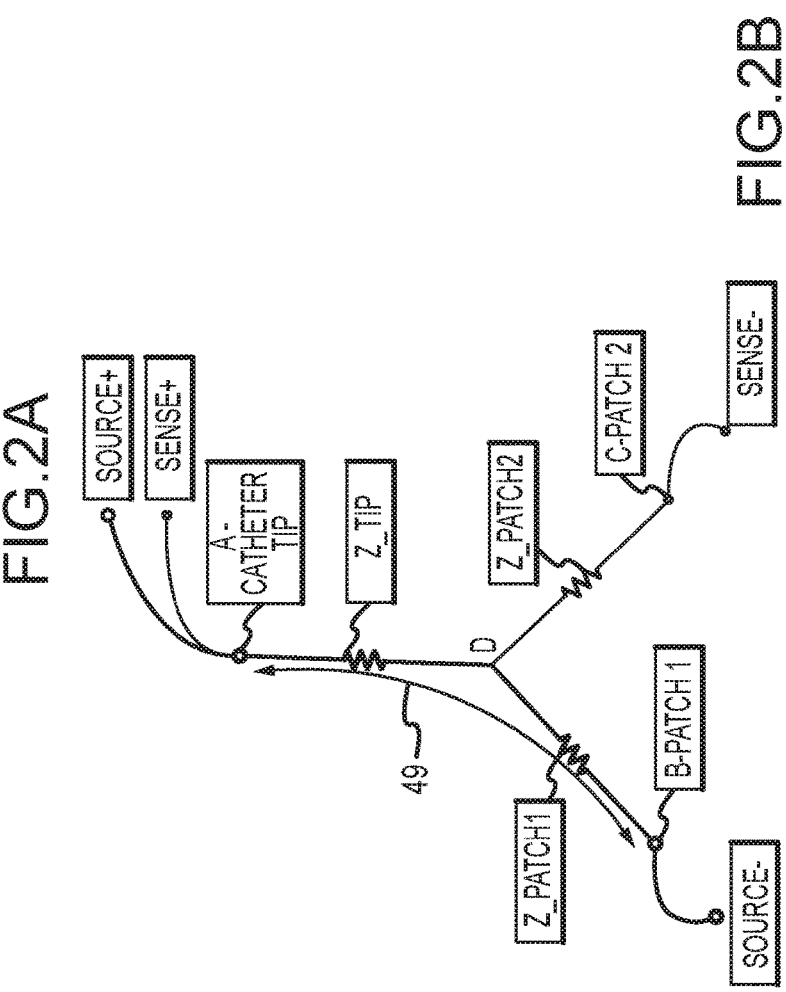
FIG. 2B is a simplified schematic diagram showing a four-wire, three-terminal approach for determining an impedance in accordance with the invention.

FIG. 2B is a simplified schematic diagram showing a further refinement of the basic concept shown in FIG. 2A. In the preferred embodiments, a 4-wire interface is used to form a three-terminal measurement arrangement. FIG. 2B shows the four wires—namely, a pair of source wires (SOURCE (+), SOURCE (−)) and a pair of sense wires (SENSE (+), SENSE (−)). These would be connected to the source and sense connectors described above. FIG. 2B also shows the three terminals: (1) a first terminal designated "A-Catheter Tip" is the tip electrode; (2) a second terminal designated "B-Patch 1" such as source return $56i$ portion of the patch 56, or a separate patch; and (3) a third terminal designated "C-Patch 2" such as the sense return $56_2$ portion of the patch 56 or a separate patch. Note, that the two separate returns (terminals) each have their own return wire. In addition to any ablation (power) signal, the present invention contemplates that an excitation signal will also be applied across the source connectors (SOURCE (+), SOURCE (−)) for the purpose of inducing a response signal with respect to the load that can be measured and which depends on the complex impedance. As described above, in one embodiment, a 20 kHz, 100 µA AC constant current signal is sourced along the path 49, as illustrated, from one tip wire (SOURCE (+) wire, starting at node A) through the tip node (node D) to the return patch (node B, SOURCE (−) wire). The complex impedance sensor 32 is coupled to the sense connectors (SENSE (+), SENSE (−)), and is configured to determine the impedance across the tip sense wire (SENSE (+)) to the return patch sense wire (SENSE (−)). For the constant current excitation signal of a linear circuit, the impedance will be proportional to the observed voltage developed across SENSE (+)/SENSE(−), in accordance with Ohm's Law: Z=V/I. Because the current flows through the path 49 only, the current through the other branch (node D to node C) due to the excitation signal is effectively zero. Accordingly, when measuring the voltage along the alternate path (between SENSE (+) and SENSE(−)), the only voltage observed will be where the two paths intersect. Depending on the location of the two patches, an ever-increasing focus will be placed on the tissue volume nearest the tip electrode. This approach results in measuring the impedance only at or near the tip electrode of the catheter when the two source/sense returns (i.e., patches) are spaced far apart.

Figure 2C:
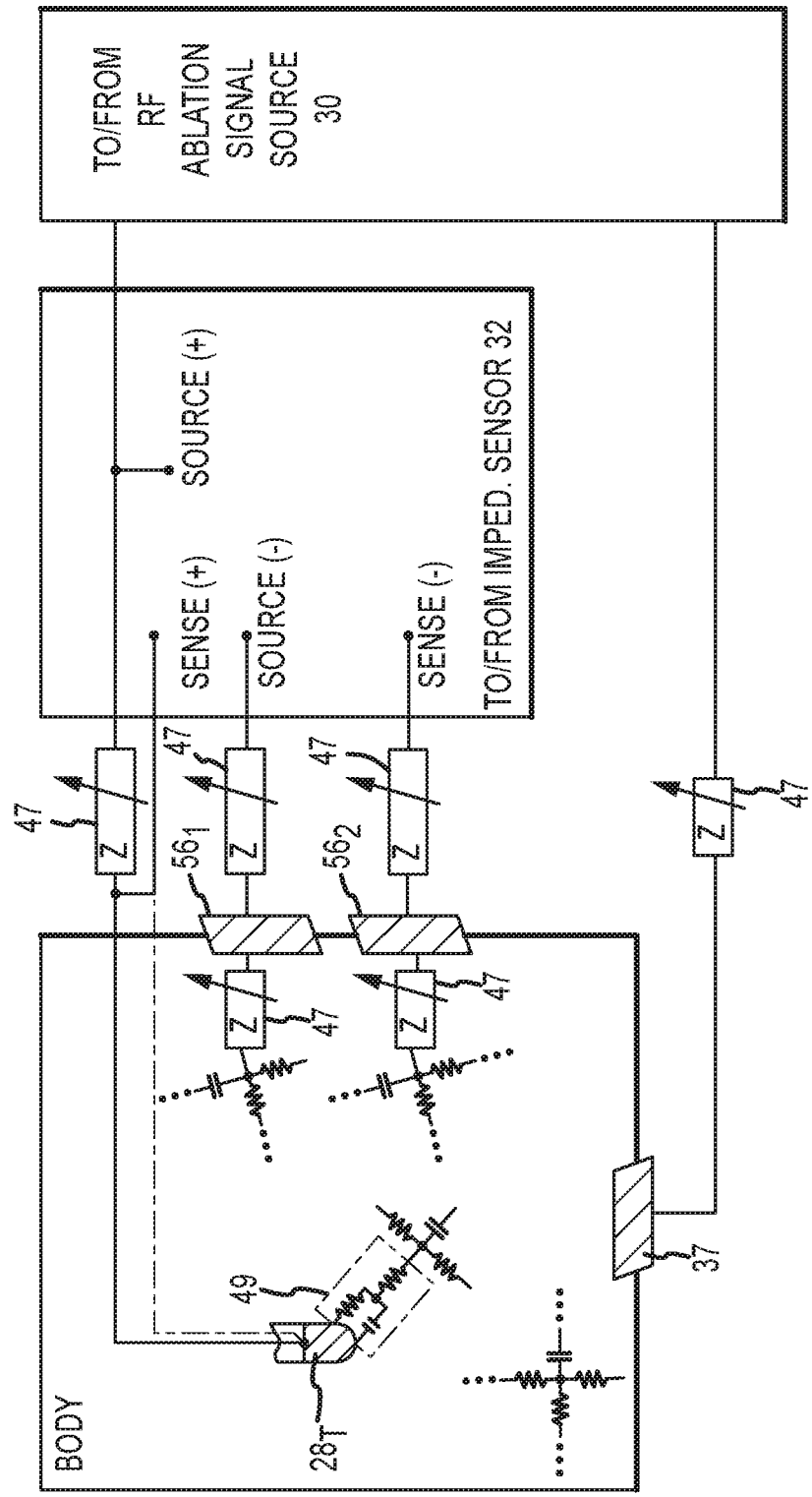
FIG. 2C is a diagrammatic and block diagram showing the four-wire, three-terminal approach of FIG. 2B in greater detail.

FIG. 2C extends the concept illustrated in FIG. 2B. FIG. 2C is a simplified schematic and block diagram of the four-wire, three-terminal measurement arrangement of the invention. For clarity, it should be pointed out that the SOURCE (+) and SENSE (+) lines joined in the catheter connector or handle (as in solid line) or may remain separate all the way to the tip electrode (the SENSE (+) line being shown in phantom line from the handle to the tip electrode). FIG. 2C shows in particular several sources of complex impedance variations, shown generally as blocks 47, that are considered "noise" because such variations do not reflect the physiologic changes in the tissue whose complex impedance is being measured. For reference, the tissue whose complex impedance is being measured is that near and around the tip electrode $28_T$, and is enclosed generally by a phantom-line box 49 (and the tissue is shown schematically, in simplified form, as a resistor/capacitor combination). One object of the invention is to provide a measurement arrangement that is robust or immune to variations that are not due to changes in or around box 49. For example, the variable complex impedance boxes 47 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 47 that are near the patches $56_1$ and $56_2$, may be more resistive/capacitive in nature, and may be due to body perspiration and the like over the course of a study. As will be seen, the various arrangements of the invention are relatively immune to the variations in blocks 47, exhibiting a high signal-to-noise (S/N) ratio as to the complex impedance measurement for block 49.

FIG. 3A is a diagrammatic view of a first embodiment of a system according to the present invention. FIG. 3A shows the catheter 12 with the ablation (tip) electrode $28_T$ at the distal end. The tip electrode $28_T$ may comprise conventional configurations as to size, shape and materials. In one embodiment, the tip electrode $28_T$ may be for example only a 2.5 mm, a 4 mm or an 8 mm length ablation electrode.

The catheter 12 include a source lead 46 (SOURCE (+)) electrically coupled to the tip electrode $28_T$ and extending through the shaft 22 to the proximal end where it is terminated. The source lead 46 is configured in this embodiment to carry the RF ablation energy and in this regard may comprise conventional materials such as insulated copper wire or the like. In one embodiment, the source lead 46 may be 32 AWG or 34 AWG copper wire.

The catheter 12 also includes a sense lead 48 (SENSE (+)) electrically coupled to the tip electrode $28_T$ and extending through the shaft 22 to the proximal end where it is terminated. The sense lead 48 is configured to allow sensing of a developed voltage across the complex impedance being measured and in this regard may comprise conventional materials, such as insulated copper wire or the like. In one embodiment, the sense lead 48 may be 38 AWG copper wire.

The leads 46 and 48 are kept electrically separate at the connector interface 18. The connector interface 18 may comprise conventional configurations known in the art for terminating electrical leads in pins or pin-receptors, or the like.

FIG. 3A also shows an optional extension cable 50 that may be included in the system 10. The cable 50 includes connectors on each end (as shown) and maintains the source and sense leads 46, 48 electrically separate throughout its length. FIG. 3A also shows a generator cable 52 having connectors at each end (as shown) and which also maintains the source and sense leads 46, 48 separate throughout its length.

FIG. 3A also shows a reference electrode wiring configuration 54, which includes a single patch 56 having multiple electrodes, namely, the source return $56_1$ (SOURCE(−)) and the sense return $56_2$ (SENSE (−)) each configured for connection to the impedance sensor 32 via respective return lines 58, 60. The return line 58 electrically connects the source return $56_1$ with the SOURCE (−) connector and the return line 60 electrically connects the sense return $56_2$ to the SENSE (−) connector. In the embodiment of FIG. 3A, the source and sense returns $56_1$ and $56_2$ are electrically isolated, but are packaged together in a single pad/patch 56, as described above. Accordingly, the distance separating them is not large, and the amount of overlap in the respective paths (see FIG. 2B discussion) is increased. FIG. 3A also shows the source and sense portions (more below in connection with FIG. 4) of the complex impedance sensor 32. Note, the pair of source connectors and the pair of sense connectors collectively define a 4-wire interface 62.

Figure 3B:
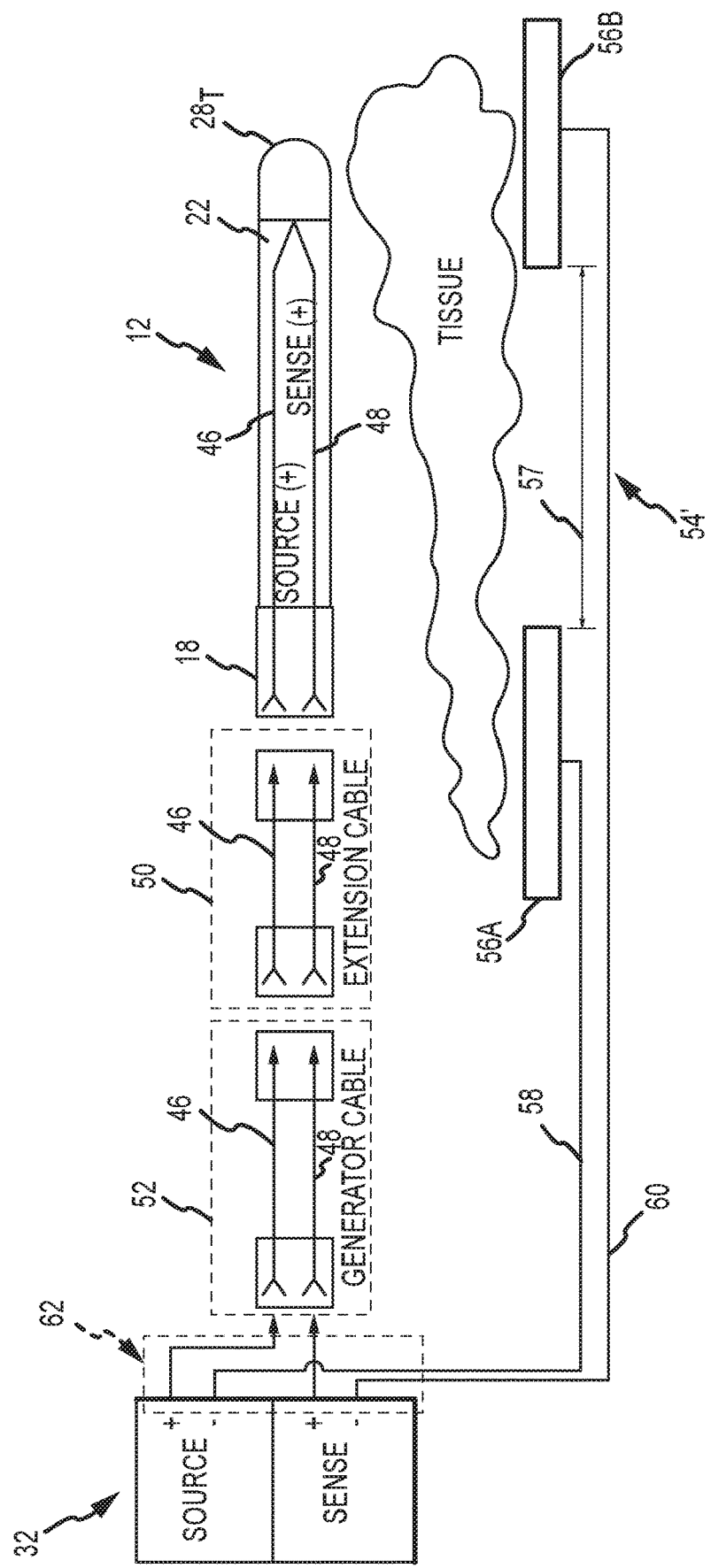
FIG. 3B is a simplified diagrammatic and block diagram of a second four-wire embodiment using a two-lead catheter and two separate patches.

FIG. 3B is a diagrammatic view of a second embodiment of the invention, which is the same as shown in FIG. 3A, except that is employs a different reference electrode wiring configuration, designated 54'. The wiring configuration 54' deploys the source and sense returns as physically separate patches 56A and 56B so as to allow independent placement of each to achieve a predetermined distance 57 between them. In a preferred embodiment, the distance 57 should be a maximum obtainable, which is typically on opposite sides of a patient (e.g., Left-Right or Front-Back). The increase in the separation distance reduces the amount of overlap between the source and sense paths and accordingly focuses the impedance measurement to just that tissue volume closest to the tip electrode, which is generally what is desired.

Figure 3C:
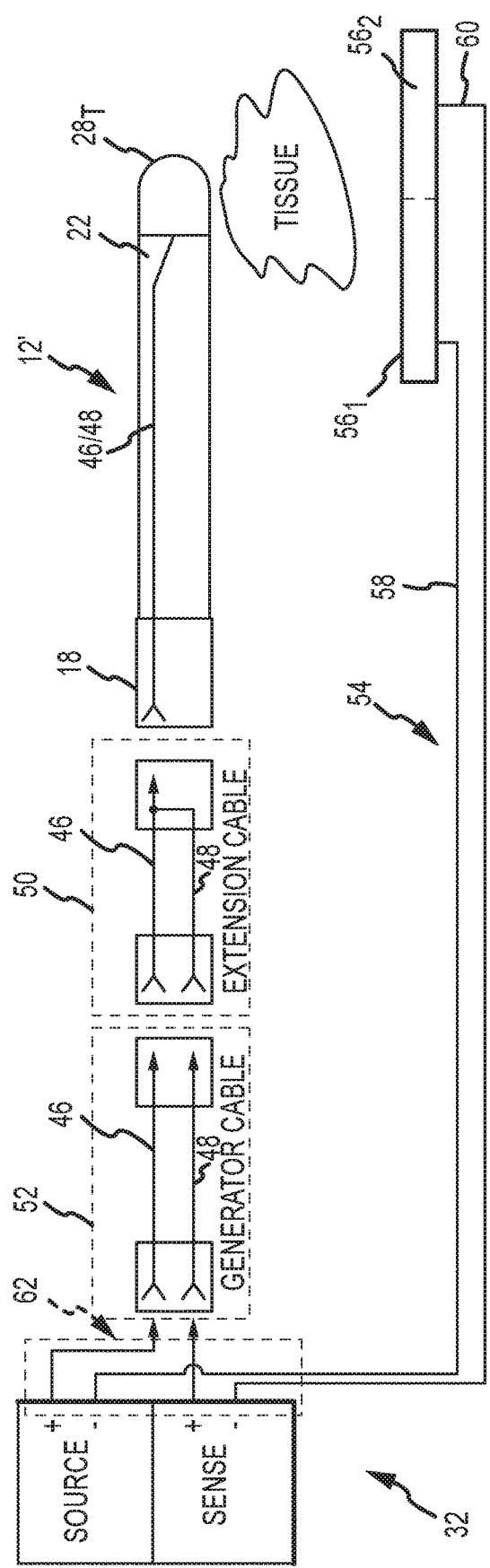
FIG. 3C is a simplified diagrammatic and block diagram of third four-wire embodiment using a single-lead catheter and the single-patch configuration.

FIG. 3C is a diagrammatic view of a third embodiment of the present invention, which is the same as the embodiment of FIG. 3A, except for a variation in the connecting cable(s) and the catheter. Particularly, an alternate catheter embodiment, catheter 12', uses a single lead, namely, a combined source/sense lead 46/48 rather than two separate leads. The combined lead is electrically connected to the tip electrode 28$_T$ and extends through the shaft 22 to the proximal end where it is terminated in the connector interface 18. The combined lead 46/48 may be of the same construction as the source lead 46 in FIG. 3A. Of the cables 50 and 52, it is contemplated that the one that is to connect to the catheter 12' will be modified. Thus, if no extension cable is used, then the generator cable 52 will be modified. If the extension cable 50 is used, then it will be modified, and the generator cable will be un-modified. More specifically, the modification involves the end connecting to the catheter 12', where the two individual, separate leads 46, 48 will be electrically joined to form a single electrical node, which is then connected to the single combined lead 46,48. It has been found that the catheter 12 (or catheter 12'), once in a patient, is not subject to the substantial environmental changes (e.g., due to coiling and the like) than can occur in the external cables 50, 52. Accordingly, a single lead through the catheter 12' is generally sufficient to combat the non-physiologic changes described herein, so long as the two separate wire approach is maintained throughout the remainder of the cabling back to the impedance sensor 32 of the ablation generator 16.

Figure 3D:
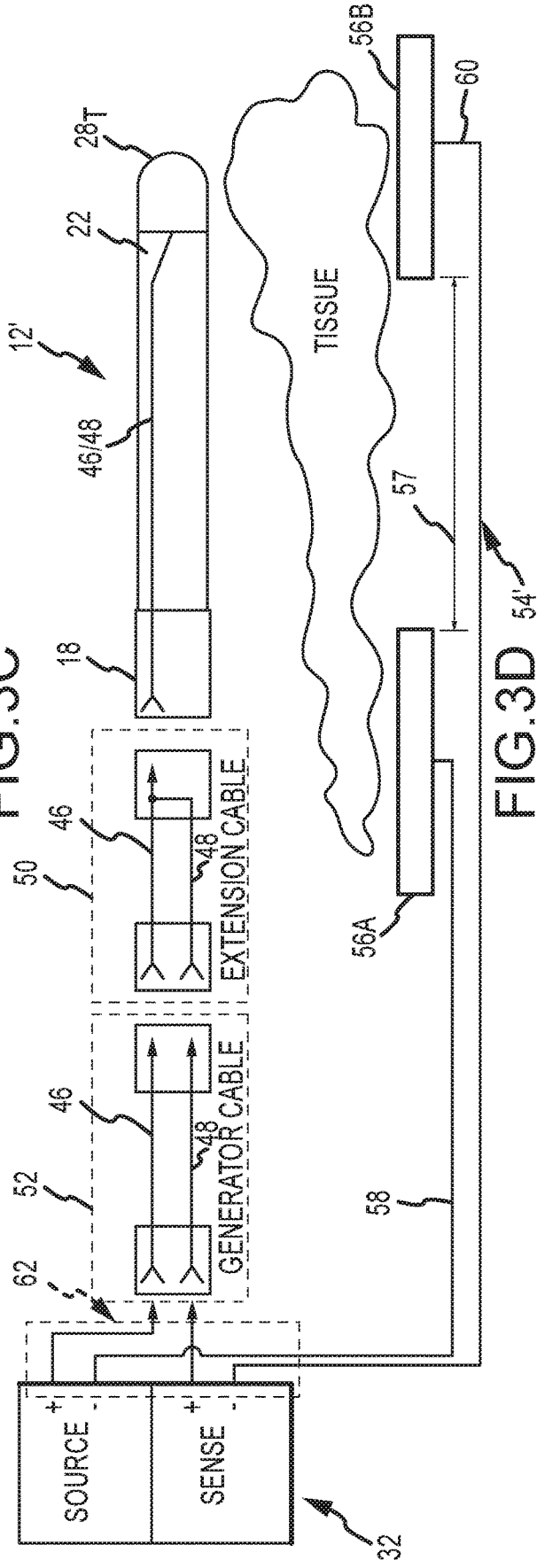
FIG. 3D is a simplified diagrammatic and block diagram of a fourth four wire embodiment using a single-lead catheter and two separate patches.

FIG. 3D is a diagrammatic view of a fourth embodiment of the present invention. FIG. 3D is the same as FIG. 3C, except that it includes the improved reference electrode wiring configuration 54' of FIG. 3B. The embodiment of FIG. 3D is the most preferred as it incorporates, in combination, the preferred reference electrode wiring configuration 54', and, it includes a very desirable commercial configuration for the catheter (i.e., one lead for impedance measurement).

Figure 3E:
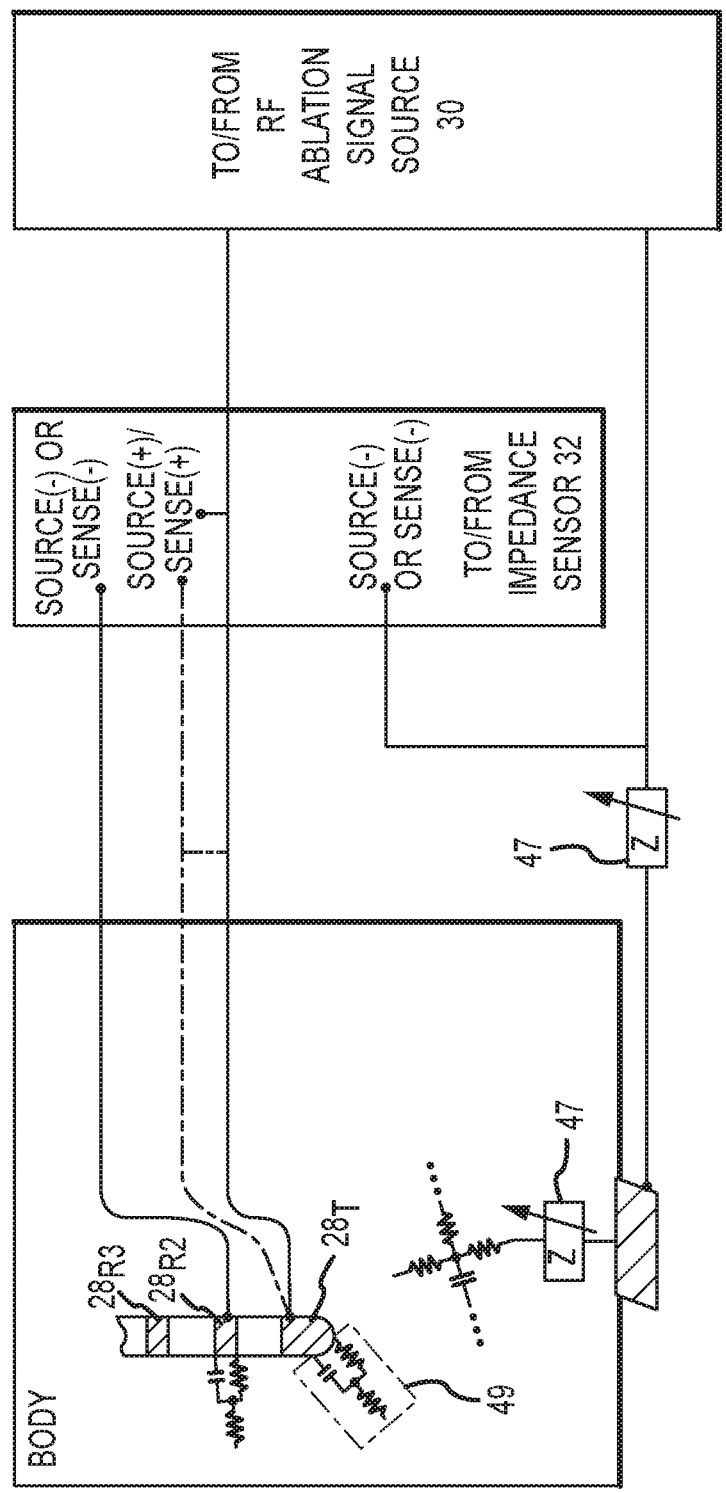
FIG. 3E is a simplified diagrammatic and block diagram of a fifth embodiment combining one of the source and sense returns with the RF indifferent return and using a ring electrode for the other one of the source/sense returns.

FIG. 3E is a diagrammatic view of a fifth embodiment of the present invention. One advantage of this embodiment is that enables complex impedance measurements using standard (i.e., existing) configurations. In the embodiment of FIG. 3E, separate patches 56A and 56B (or even the single patch 56) are not used for the source and sense returns. Rather, one of the source or sense returns is combined with the RF indifferent return 37 while the other one of the source or sense returns is coupled to the Ring-2 electrode 28$_{R2}$. In the illustrated embodiment, the source (+) and sense (+) wires are electrically joined at the complex impedance sensor 32 and are carried, through any intervening cables and through the catheter handle/shaft to the tip electrode 28$_T$ using a single wire (as shown). In an alternate embodiment, however, separate wires for the source (+) and sense (+) may be used up to the catheter handle, then joined. In a still further embodiment, individual wires for source (+) and sense (+) may be kept separate all the way to the tip electrode. These last two wiring alternatives (i.e., joined in the handle, or joined at the tip electrode) are shown in phantom-line fashion. This variation provides immunity to non-physiologic variations (blocks 47), and hence accurate complex impedance measurements, while offering an attractive commercial implementation (i.e., uses conventional equipment configurations).

Figure 4:
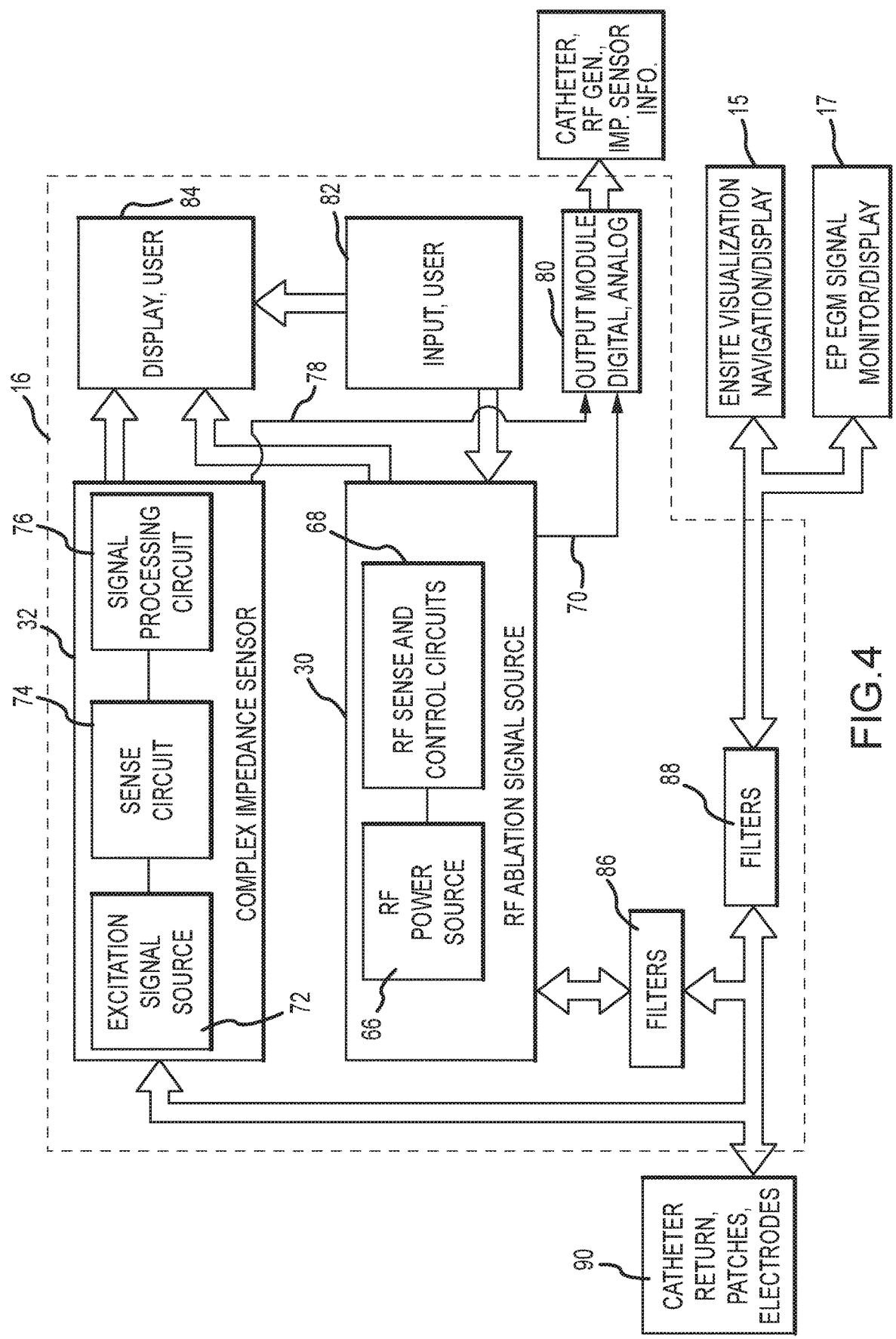
FIG. 4 is a block diagram of an RF ablation generator according to the invention.

FIG. 4 is a simplified block diagram showing, in greater detail, the exemplary ablation generator 16 of FIG. 1, including and integrating the complex impedance sensor 32. In general, the ablation generator and complex impedance sensor functions are known in the art, and can be implemented by modifying known approaches according to the teachings of the present invention. However, for the sake of completeness, a brief description will be given.

FIG. 4 shows that the RF ablation signal source 30 includes an RF power source 66 and RF sense and control circuits block 68, which are configured to cooperate to produce the RF ablation signal (destined for block 90). The RF power source 66 is configured to generate the signal at a predetermined frequency in accordance with one or more user specified parameter (e.g., power, time, etc.), as well known in the art, under the control of the RF sense and control circuits 68. The block 30 is configured to generate various operating information 70 for output to an output module 80. In general, blocks 66 and 68 may comprise conventional apparatus, as described above.

The complex impedance sensor 32 includes an excitation signal source 72, a sense circuit 74 and a signal processing circuit 76. The excitation signal source 72 is configured to generate the excitation signal across the SOURCE (+)/ SOURCE (−) connectors of the generator 16 at the predetermined frequency, as described in detail above. The excitation signal is provided to block 90 for output at the SOURCE (+)/SOURCE (−) connectors. The sense circuit 74 is configured to measure the response signal induced by the excitation signal as observed across the SENSE (+)/SENSE (−) connectors of the generator 16 (by way of block 90). Additionally, the sense circuit 74 includes filtering (not shown) configured to block frequencies not of interest and allow frequency of interest, for example at the excitation frequency, to pass (i.e., a band pass). The signal processing circuit 76 is configured to process the response signal, based on the excitation signal, to determine the complex impedance of the subject tissue near and/or around the tip electrode. In general, the complex impedance sensor 32 is configured to output various operating information 78 (e.g., including the determined complex impedance) for output to the output module 80. The excitation source 72, sense circuit 74 and signal processing circuit 76 may comprise conventional apparatus known in the art.

The output module 80 is configured to provide a digital and analog signal interface to various external apparatus, for providing catheter, RF generator and complex impedance sensor information. The user input block 82 is configured to receive input parameters from a user of the RF ablation generator 16, such as desired power, time and the like, all as known in the art. The user display 84 is configured to display various operating information of the ablation generator 16, for example, present power level, time, tissue temperature, and impedance (complex impedance).

The ablation generator 16 includes a first blocking filter block 86 and a second blocking filter block 88, each of which is series resonant at the RF ablation signal frequency and parallel resonant at the excitation signal frequency. These filtering blocks allow signals in the frequency band of interest to pass to the appropriate block (e.g., EGM signals to pass through to the EGM display).

Block 90 represents the connectors and interface generally to the catheter, RF indifferent return, the source and sense returns (patches) and the catheter electrodes.

Figure 5:
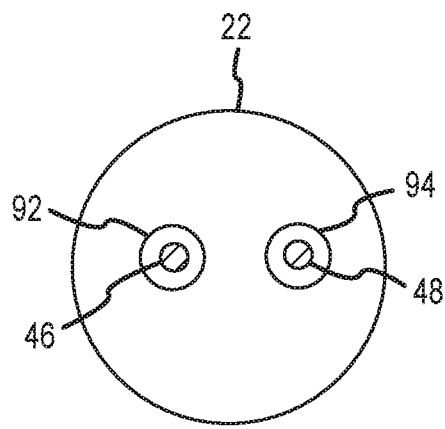
FIG. 5 is a cross-sectional view of a two-lead catheter having a separate lumen for each lead.

FIG. 5 is a simplified cross-sectional view of the catheter 12. In the embodiments of FIGS. 3A-3B where the catheter 12 includes separate source and sense leads 46, 48 extending throughout, in one embodiment, a first lumen 92 is provided for the source lead 46 and a second lumen 94 is provided for the sense lead 48. This embodiment keeps the two leads apart and electrically separated in separate lumens.

Figure 6:
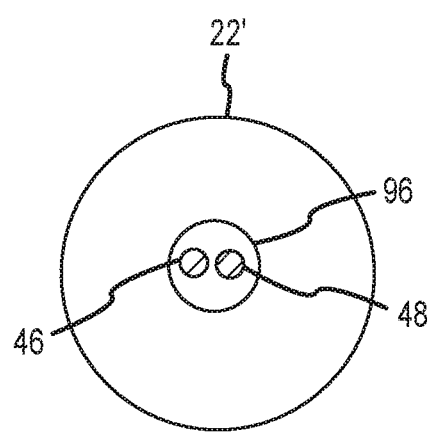
FIG. 6 is a cross-sectional view of a two-lead catheter having a single lumen configured for both leads.

FIG. 6 is a simplified cross-sectional view of the catheter 12. In the embodiments of FIGS. 3A-3B where the catheter 12 includes separate source and sense leads 46, 48 extending throughout, in another embodiment, a lumen 96 is provided that is configured in size to accommodate both leads 46, 48. Note, in this embodiment, the leads 46, 48 are not electrically in contact (i.e., they would be electrically insulated from each other).

Figure 7:
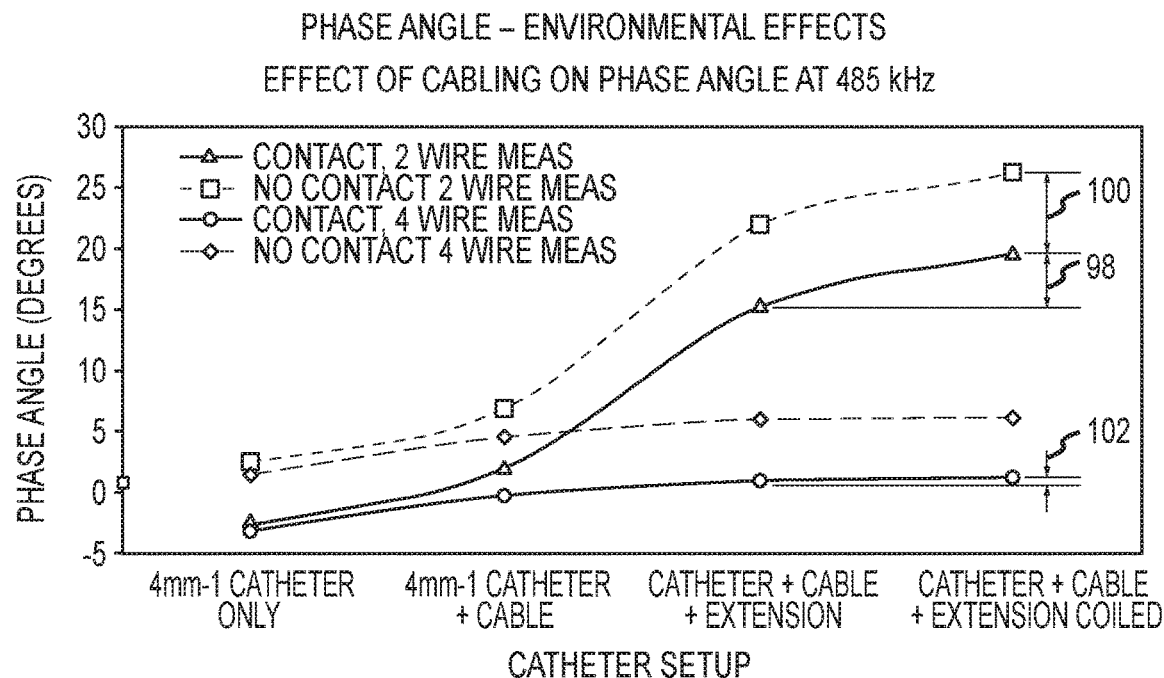
FIG. 7 is diagram comparing variations in phase angle as a function of catheter setup both with and without the features of the present invention.

FIG. 7 is a diagram comparing variations in phase angle as a function of catheter setup, both with and without the features of the present invention. The diagram shows traces for both the conventional 2-wire approach as well as for the inventive 4-wire (3-terminal) approach. In addition, there are corresponding traces, for both 2-wire and 4-wire approaches, reflecting instances where the tip electrode is in contact with the tissue, and where the tip electrode is not in contact with the tissue. As known, one variable in measuring complex impedance with any approach involves whether or not the tip electrode is (or is not) in contact with the tissue for which the impedance measurement is being taken. For purposes of FIG. 7, the "No Contact" situation corresponds to an approximately 20 mm spacing between the tip electrode and the tissue surface, while the "Contact" situation corresponds to the tip electrode just touching the surface (i.e., as determined visually) and then with a further 1 mm movement of the tip electrode into the tissue.

As FIG. 7 shows, there is an approximately 3° phase angle shift, designated by reference numeral 98, between the "Catheter+Cable+Extension" setup and the "Catheter+Cable+Extension Coiled" setup at 485 kHz using the conventional 2-wire measurement method. This scenario is a common, since the difference between the setups is just the coiling of an extension cable. FIG. 7 also shows that there is an approximately 6° phase angle between "Contact" and "No Contact" for a "Catheter+Cable+Extension Coiled" setup, designated by reference numeral 100. Absent correction, the simple rearrangement/coiling of cables and the like could be falsely reported to the doctor/practitioner as a change in phase angle. Finally, FIG. 7 show a nearly negligible phase angle change, designated by reference numeral 102, between the "Catheter+Cable+Extension" setup and the "Catheter+Cable+Extension Coiled" setup at 485 kHz using the inventive 4-wire measurement method. Similar improvement with respect to magnitude are also provided by the present invention, described below.

Figure 8:
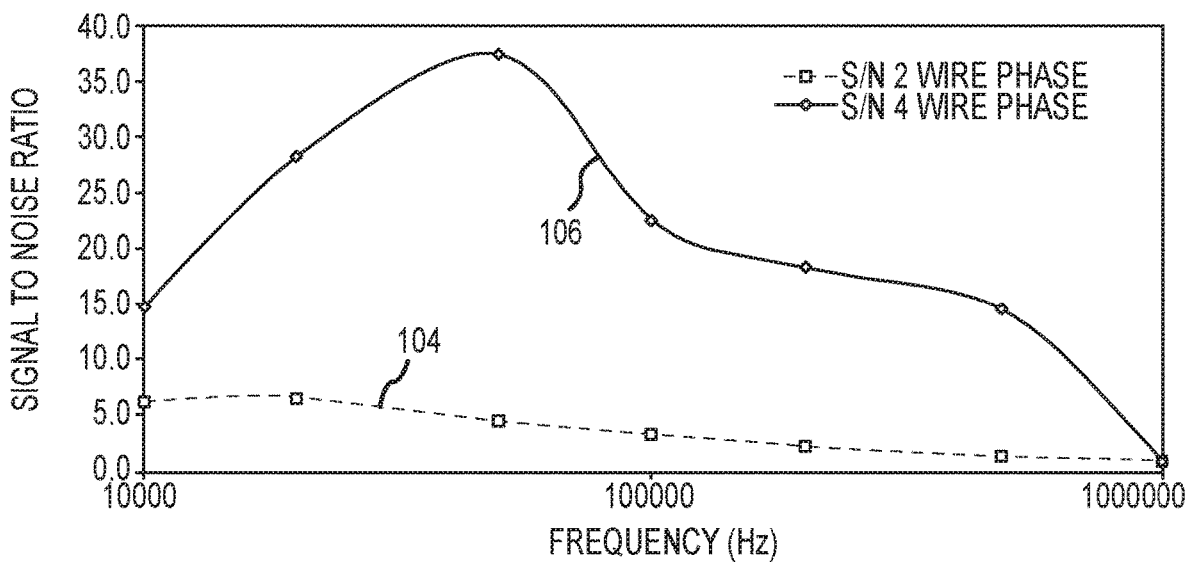
FIG. 8 is a diagram showing a signal-to-noise ratio as a function of frequency and comparing a conventional two-wire approach in one trace with the present invention in a second trace.

FIG. 8 is a diagram showing a signal-to-noise (S/N) ratio as a function of frequency and comparing a conventional 2-wire approach in one trace with the inventive 4-wire, 3-terminal measurement approach in a second trace. In FIG. 8, the signal used in the S/N computation corresponds to the contact-no contact measured levels, while the noise component corresponds to a cable-to-coiled cable measured levels. The conventional 2-wire S/N ratio, shown as trace 104, is relatively low, indicating possible difficulties distinguishing true signal from noise (here, changes attributable to non-physiologic changes in a patient). On the other hand, the S/N ratio of the inventive 4-wire approach, shown as trace 106, is relatively large over a broad frequency range, indicating a substantial improvement in robustness and immunity to non-physiologic changes that could cause a monitoring apparatus to falsely report phase and/or magnitude changes.

Figure 9:
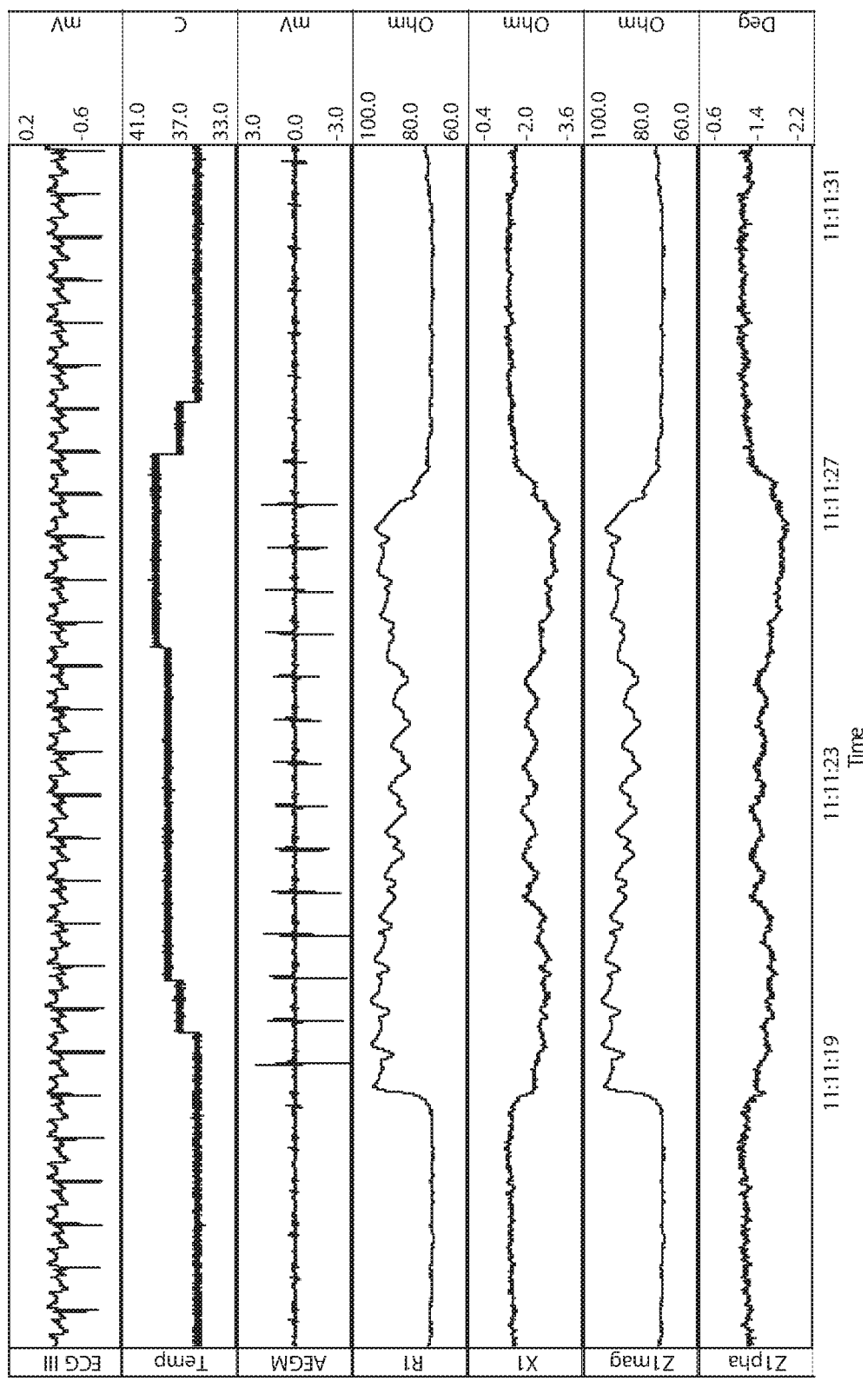
FIG. 9 is a series of timing diagrams illustrating complex impedance variations during atrial tissue ablation.

FIG. 9 is a series of timing diagrams (in registration with each other) illustrating impedance signal changes obtained during ablation catheter manipulation in accordance with the present invention. RF energy was continuously applied at 20 watts through an irrigated catheter. With atrial tissue contact, the irrigated catheter temperature rises slightly (see trace labeled "Temp") and the atrial electrogram (trace labeled "AEGM") signal's amplitude increases. The 4-wire, 3-terminal impedance sensor's response is seen in terms of resistance, reactance, complex impedance magnitude and phase angle, shown in signals labeled "R1", "X1", "Z1mag" and "Z1pha", respectively. The resistance and impedance magnitude increase by twenty (20) or so ohms whereas capacitive reactance and phase angle becomes more negative.

Table 1 (below) shows data taken from testing that quantifies the "noise" immunity advantages of the present invention. In particular, Table 1 reflects tissue coupling measurements and model elements derived from studies in a set of six (6) anesthetized pigs. Measurements were made from a set of 2- and 3-terminal configurations to compare conventional 2-terminal tip-to-patch measurements (Za+Zb or Za+Zc) with the 3-terminal measurement of this invention (Za). In this regard, note that the complex impedance notation (i.e., Za, Zb, Zc) described here is taken from and with respect to the simplified schematic diagram of FIG. 2B (viz., in FIG. 2B, Za is called out as Z_TIP, Zb is called out as Z_PATCH1 and Zc is called out as Z_PATCH2).

TABLE 1

| Electrode | Element | Mean I, NC | | MeanΔ I, C-NC | | MeanΔ F-I, NC | | MeanΔ I, NC, Pswap | |
|---|---|---|---|---|---|---|---|---|---|
| | | R | X | R | X | R | X | R | X |
| Tip 4 mm | Za | 82.7 | −3.1 | 32.1 | −2.3 | −2.6 | 0.8 | 0.1 | 0.1 |
| Patch 8 × 15 cm | Zb | 24.7 | −34.1 | −0.4 | 0.4 | −4.7 | 7.1 | | |
| Patch 4.5 × 9.5 cm | Zc | 71.4 | −67.3 | 0.8 | 0.2 | −2.5 | 2.3 | | |
| | Za + Zb | 107.4 | −37.1 | 31.6 | −1.9 | −7.3 | 7.9 | 46.7 | −33.2 |
| | Za + Zc | 154.1 | −70.3 | 32.8 | −2.1 | −5.1 | 3.1 | −46.7 | 33.2 |

As mentioned above, empirical evidence was obtained quantifying the advantages of the invention in characterizing catheter-tissue contact or coupling from a series of six (6) anesthetized animals. In the course of these studies, a Seven French (7 Fr) ablation catheter with a 4 mm open irrigated tip electrode was placed in the right atrium and two patch electrodes (one 8×15 cm and one 4.5×9.5 cm) were placed on the posterior-lateral flank region, which acted as the "source return" and "sense return" as described elsewhere herein. A series of 2- and 3-terminal impedance measurements were made at 20 kHz at the beginning (designated "I")

and end (designated "F") of each study and with the catheter tip in both non-contact (designated "NC") and contact (designated "C") conditions.

The 3-terminal 4-wire method disclosed here produces a direct measurement of equivalent circuit impedance element Za belonging to the tip electrode. A conventional 2-terminal 2-wire method measures the sum of impedance elements Za+Zb or Za+Zc, depending on the patch electrode selected. Selected measurements were also made with the two patches interchanged or swapped (designated "Pswap") to assess sensitivity to patch type, size, and location in this set of animals. A 3-terminal, linear, equivalent circuit capable of reproducing all possible 2- and 3-terminal impedance measurements has Y-element complex impedances shown in Table 1 under the column heading Mean I, NC (for mean, initial, and non-contact).

Each of the subject's models were obtained again when the tip electrode was in contact with atrial tissue. The model element changes are shown in the column labeled MeanΔ I, C-NC (for mean, initial, contact-non-contact). These changes represent a contact or tissue coupling signal and are seen as mostly resistive (about 32 ohms) and almost entirely attributed to the tip associated impedance element, Za. The study also incorporated two estimates of noise, one obtained from measurements over the course of each study (a mean duration of 5.3 hrs) and the other from swapping the two patches to estimate patch-to-patch variation. Patch type, size, and location contributed some 30-40 ohms of resistance and reactance change but almost no measurable tip change (0.1 ohms).

From this information an estimate of signal to noise ratio was derived, as seen in Table 2 (below). Since the signal was predominantly resistive, this analysis focused on a resistive index of signal to noise. To simulate the combined variation possible, we added the absolute values of the mean final-initial changes to the swap patch changes. The result shows the invention to be significantly more robust to tip-tissue contact than a conventional measurement approaches.

TABLE 2

| Type | Element | Signal R | Noise R | S/N Ratio R |
|---|---|---|---|---|
| 3-term | Za | 32.1 | 2.7 | 12.0 |
| 2-term | Za + Zb | 31.6 | 54.0 | 0.6 |

Table 2 specifically provides a quantitative comparison of the performance of the 3-terminal, 4-wire measurement described in this invention with a conventional 2-terminal Tip-to-patch measurement. The Table 2 data shows that atrial tissue contact resistance rises on average about 32 ohms in each case, but that temporal and patch-patch variation can contribute nearly twice as much to a 2-terminal measurement. The 3-terminal measurement, by isolating the tip from the combined tip+patch system, is only modestly influenced by patch type and time.

The impedance sensing approach of the invention may also be deployed independent of the illustrated, exemplary embodiment (RF ablation generator). For example, the complex impedance measuring approach may be deployed instead in the context of cryoablation or other means to treat arrhythmias or even without direct means to treat cardiac disease. It may also be applied to procedures or locations outside the heart.

One advantage of the present invention is its immunity to "non-physiologic" fluctuations of impedance due either to cable or wiring variables as well as variations in patch electrode to tissue interface impedance. Instead, the complex impedance sensing approach responds predominantly to physiologic and anatomic changes in the tip electrode to tissue interface.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology catheter system, comprising:
   a catheter having an elongated shaft configured for intracardiac use and having a proximal end and a distal end, a first electrode disposed at said distal end, a second electrode proximal of said first electrode, wherein said second electrode comprises a ring electrode, a first sense lead electrically connected to said first electrode and extending through said shaft to said proximal end, and a second sense lead, different from said first sense lead, electrically connected to said second electrode and extending through said shaft to said proximal end;
   an excitation signal source coupled to said catheter configured to produce an excitation signal comprising an electrical current proximate said first electrode;
   a sense circuit coupled to said first and second electrodes by way of said first and second sense leads configured to measure a response signal induced by said excitation signal as observed across said first and second electrodes; and
   a processing circuit configured to process said response signal, based on the excitation signal, to determine an impedance of a cardiac tissue volume proximate said first electrode to treat a cardiac arrhythmia.

2. The catheter system of claim 1 wherein said first and second sense leads are configured for connection to an impedance sensor.

3. The catheter system of claim 2 wherein said impedance sensor comprises a complex impedance sensor and said determined impedance of the cardiac tissue volume comprises a complex impedance.

4. The catheter system of claim 2 wherein said impedance sensor includes said excitation signal source circuit configured to produce said excitation signal.

5. The catheter system of claim 1 wherein said excitation signal comprises an alternating current (AC) signal having a first frequency between about 2 kHz and 200 kHz.

6. The catheter system of claim 5 wherein said first frequency is about 20 kHz.

7. The catheter system of claim 5 wherein said excitation signal comprises a constant current AC excitation signal configured to develop a corresponding AC response voltage signal.

8. The catheter system of claim 1 wherein said excitation signal comprises a constant current signal in a range of between about 20-200 µA.

9. The catheter system of claim 8 wherein said constant current signal comprises a current of about 100 µA.

10. The catheter system of claim 1 wherein said first and second sense leads comprise insulated copper wire.

11. The catheter system of claim 1 wherein said catheter comprises a third electrode proximal of said second electrode wherein said third electrode comprises a ring electrode.

12. A method of determining an impedance of a cardiac tissue volume, comprising:
   providing an electrophysiology catheter with an elongated shaft configured for intra-cardiac use and having a proximal end and a distal end, a first electrode disposed at the distal end, a second electrode proximal of the first electrode, wherein the second electrode comprises a ring electrode, wherein providing the catheter further comprises:
      providing a first sense lead electrically connected to the first electrode and extending through the shaft to the proximal end; and
      providing a second sense lead, different from the first sense lead, electrically connected to the second electrode and extending through the shaft to the proximal end wherein providing the catheter further includes configuring the first and second sense leads for connection to an impedance sensor;
   producing an excitation signal comprising an electrical current proximate the first electrode;
   measuring, between the first and second electrodes, a response signal induced by the excitation signal as observed across the first and second electrodes; and
   processing the response signal, based on the excitation signal, to determine an impedance of the cardiac tissue volume.

13. The method of claim 12 wherein producing the excitation signal is performed by an excitation signal source in the impedance sensor.

14. The method of claim 12 wherein producing the excitation signal further comprising generating an alternating current (AC) signal having a first frequency between about 2 kHz and 200 kHz.

15. The method of claim 14 further comprising generating the AC signal having the first frequency about 20 kHz.

16. The method of claim 12 wherein producing the excitation signal comprises generating a constant current signal in a range of between about 20-200 µA.

17. The method of claim 16 wherein the constant current signal comprises a current of about 100 µA.

18. The method of claim 12 wherein providing the first and second sense leads further comprises configuring the first and second sense leads so as to comprise insulated copper wire.

19. The method of claim 12 wherein providing the catheter further comprises providing a third electrode proximal of the second electrode.

* * * * *